United States Patent
Perez-Cruet et al.

(10) Patent No.: US 7,896,904 B2
(45) Date of Patent: Mar. 1, 2011

(54) VERTEBRAL DISC TENSIONING DEVICE

(75) Inventors: Miguelangelo J. Perez-Cruet, Bloomfield, MI (US); John R. Pepper, Cheshire, CT (US)

(73) Assignee: Mi4Spine, LLC, Bloomfield Hills, MI (US)

( * ) Notice: Subject to any disclaimer, the term of this patent is extended or adjusted under 35 U.S.C. 154(b) by 0 days.

(21) Appl. No.: 12/492,909

(22) Filed: Jun. 26, 2009

(65) Prior Publication Data
US 2009/0259258 A1 Oct. 15, 2009

Related U.S. Application Data

(63) Continuation-in-part of application No. 11/646,750, filed on Dec. 28, 2006, now Pat. No. 7,666,211.

(51) Int. Cl.
*A61B 17/70* (2006.01)
(52) U.S. Cl. .................. 606/257; 606/246
(58) Field of Classification Search ......... 606/300–321, 606/246, 248, 250–279; 623/17.11
See application file for complete search history.

(56) References Cited

U.S. PATENT DOCUMENTS 7,559,942 B2 * 7/2009 Paul et al. .................. 606/250
2004/0260283 A1 * 12/2004 Wu et al. ..................... 606/61

* cited by examiner

*Primary Examiner*—Eduardo C Robert
*Assistant Examiner*—Christina Negrelli
(74) *Attorney, Agent, or Firm*—John A. Miller; Miller IP Law, PLC

(57) ABSTRACT

A vertebral disc tensioning device that restores the loss of disc height as a result of disc degeneration and other factors. The device includes first and second pedicle screws each including a screw body portion and a ball head. The device also includes first and second screw head portions each including an internal threaded bore where the first screw is inserted in the first screw head portion and is pivotally mounted relative thereto and the second screw is inserted in the second screw head portion and is pivotally mounted thereto. The device also includes a rigid connector that couples the first and second screw head portions where bolts are threaded through the connector and into the internal threaded bores of the first and second screw head portions. The device also includes a spring assembly offset from the rigid connector that applies a bias to separate the pedicle screws.

25 Claims, 11 Drawing Sheets

VERTEBRAL DISC TENSIONING DEVICE

CROSS-REFERENCE TO RELATED APPLICATIONS

This application is a continuation-in-part application of U.S. patent application Ser. No. 11/646,750, filed Dec. 28, 2006, titled "Vertebral Disc Annular Fibrosis Tensioning and Lengthening Device."

BACKGROUND OF THE INVENTION

1. Field of the Invention

This invention relates generally to a vertebral disc tensioning device and, more particularly, to a vertebral disc tensioning device that includes a pair of pedicle screws, screw head portions coupled to each screw, a rigid connector connecting the screw head portions and a spring member applying a bias to gradually separate the pedicle screws to restore disc space height over time.

2. Discussion of the Related Art

The human spine includes a series of vertebrae interconnected by connective tissue referred to as intervertebral discs that act as a cushion between the vertebrae. The discs allow for movement of the vertebrae so that the spine can bend and rotate.

The intervertebral disc is an active organ in which the normal and pathologic anatomies are well known, but the normal and pathologic physiologies have not been greatly understood. The intervertebral disc permits rhythmic motions required of all vertebrate animals in their various forms of locomotion. The disc is a high-pressure system composed primarily of absorbed water, an outer multilayered circumferential annulus of strong, flexible, but essentially inelastic collagen fibers, and an inner core of a hydrogel called the nucleus pulposus. The swelling of the contained hydrogel creates the high pressure that tightens the annular fibers and its laminations. Degeneration of discs in humans is typically a slow, complex process involving essentially all of the mechanical and physiologic components with loss of water holding capacity of the disc. Discogenic pain arises from either component, but is primarily due to altered chemistry. When this pain is severely disabling and refractory to non-operative, the preferred contemporary treatments are primarily surgical, particularly fusion and/or disc replacement.

Annular collagen fibers are arranged in circumferential belts or laminations inserting strongly and tangentially in right- and left-handed angulated patches into each adjacent vertebral body. Inside the annular ring is contained an aggrecan, glycosaminoglycan, a protein-sugar complex gel having great hygroscopic ability to hold water. The swelling pressure of this gel of the nucleus maintains the pressure within the annulus, forcing the vertebrae apart and tightening the annular fibers. This tightening provides the primary mechanical stability and flexibility of each disc of the spinal column. Further, the angulated arrangement of the fibers also controls the segmental stability and flexibility of the motion segment. Therefore, the motion of each segment relates directly to the swelling capacity of the gel and secondarily to the tightness of intact annulus fibers. The same gel is also found in thin layers separating the annular laminar construction, providing some apparent elasticity and separating the laminations, reducing interlaminar torsional abrasion. With aging or degeneration, nucleus gel declines, while collagen content, including fibrosis, relatively increases.

Disc degeneration, which involves matrix, collagen and aggrecan, usually begins with annular tears or alterations in the endplate nutritional pathways by mechanical or pathophysiological means. However, the disc ultimately fails for cellular reasons. As a person ages, the discs in the spine go through a degenerative process that involves the gradual loss of the water holding capacity of the disc, referred to as desiccation. As a result of this loss of water, the disc space height may partially collapse, which may lead to chronic back pain disorders and/or leg pain as a result of the nerves being pinched.

Progressive injury and aging of the disc occurs normally in later life and abnormally after trauma or metabolic changes. In addition to the chemical effects on the free nerve endings as a source of discogenic pain, other degenerative factors may occur. Free nerve endings in the annular fibers may be stimulated by stretching as the disc degenerates, bulges, and circumferential delamination of annular fibers occurs. This condition may lead to a number of problems. It has been shown that a person's disc is typically thicker in the morning when a person awakes. This phenomenon may be due in part to the reduction of body weight forces on the disc when lying in a recumbent position overnight that causes the disc height to restore. Therefore, the reduction of compressive forces on the disc may help to restore disc height.

As discussed above, as a person ages, the discs of the spine degenerate, and the disc space height collapses. Further, the ligaments and facets of the spine degenerate as well due to increased forces and stresses on these structures that occur as the disc loses its weight-bearing capacity. These problems lead to a reduction in the foramenal height of the vertebrae, often causing central or lateral canal stenosis. The foramen is an opening through the vertebrae that allows the nerve from the spinal cord to pass through. Because the nerve passes through the foramen, the nerve will often get pinched as the disc height decreases, leading to various types of back pain. Further, these problems often lead to difficulty in walking. Additionally, the lateral canal stenosis causes the nerve to get pinched in the spinal canal. These conditions often lead to neurogenic claudication, where the patient typically responds by walking shorter distances, then sitting down, and then flexing the spine by leaning over or by walking with the aid of a device, which helps to flex the spine.

The treatment of degenerative disc disease and associated spine ailments is one of the most costly medical conditions with an estimated annual direct cost in the United States of thirty-three billion dollars and a total annual societal cost exceeding one hundred billion dollars. Indeed, in one's lifetime most individuals will experience an episode of significant back and/or neck pain.

SUMMARY OF THE INVENTION

In accordance with the teachings of the present invention, a vertebral disc tensioning device is disclosed that restores the loss of disc height as a result of disc degeneration and other factors. In one embodiment, the device includes first and second pedicle screws each including a screw body portion and a ball head. The device also includes first and second screw head portions each including an internal threaded bore where the first screw is inserted in the first screw head portion and is pivotally mounted relative thereto and the second screw is inserted in the second screw head portion and is pivotally mounted thereto. The device also includes a rigid connector that couples the first and second screw head portions where bolts are threaded through the connector and into the internal threaded bores of the first and second screw head portions.

The device also includes a spring assembly offset from the rigid connector that applies a bias to separate the pedicle screws.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a vertebral disc tensioning device is merely exemplary in nature, and is in no way intended to limit the invention or its applications or uses.

Figure 1:
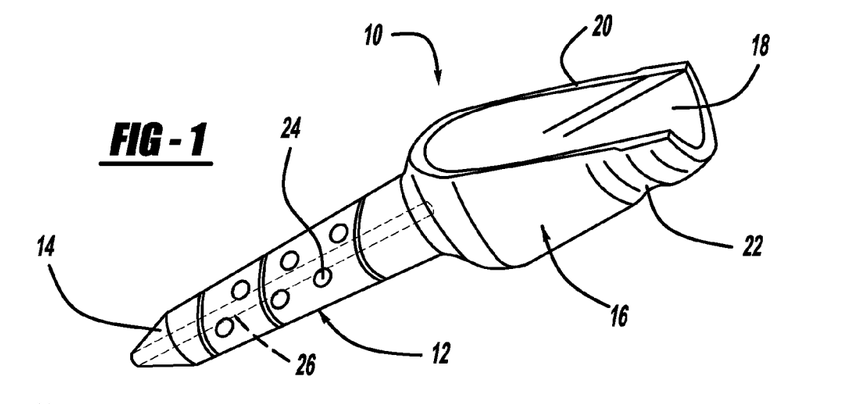
FIG. 1 is a perspective view of a pedicle screw employed in a vertebral disc annular fibrosis tensioning and lengthening device.
Figures 2, 3:
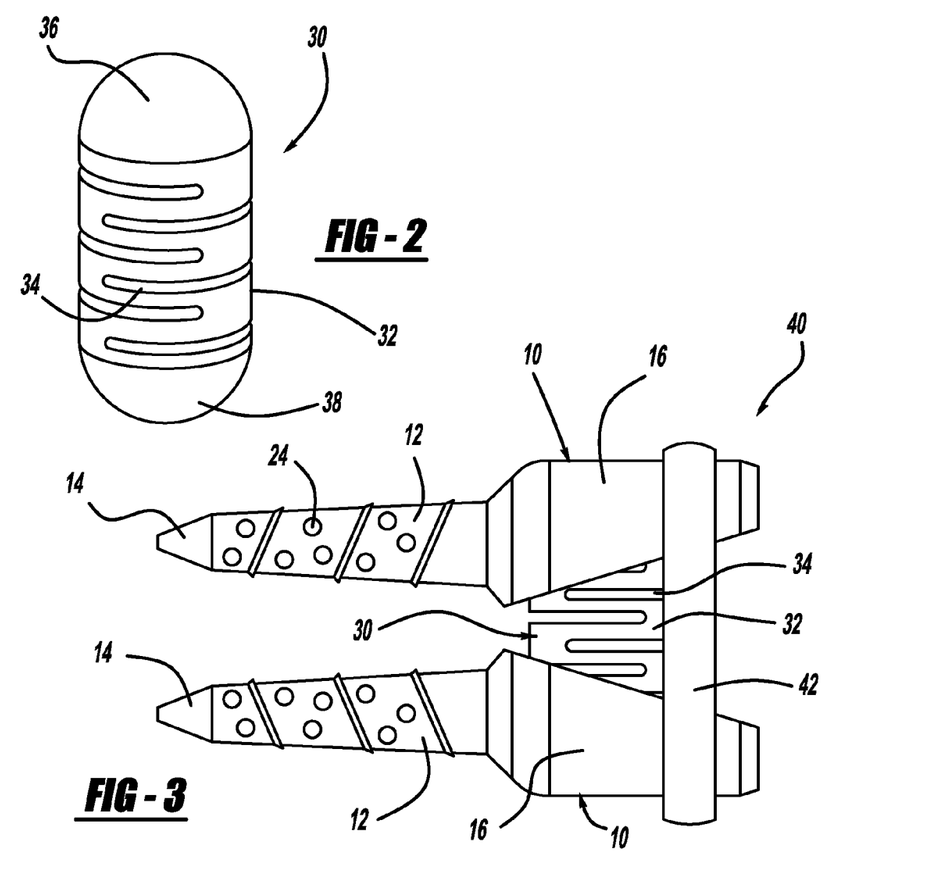
FIG. 2 is a perspective view of a spring employed in the vertebral disc annular fibrosis tensioning and lengthening device.
FIG. 3 is a side view of the vertebral disc annular fibrosis tensioning and lengthening device of the invention including two of the pedicle screws with the spring therebetween.

FIG. 1 is a perspective view of a pedicle screw 10 for use in a vertebral disc annular fibrosis tensioning and lengthening device (FIG. 3). The pedicle screw 10 includes a threaded and tapered body portion 12 having a tip 14. The body portion 12 includes a plurality of holes 24 that allow bone to grow therein when the screw 10 is threaded into the vertebral body so that the pedicle screw 10 is better anchored within the vertebra. The use of holes in the body portion of a pedicle screw to facilitate bone growth therein can be employed in other types of pedicle screws for other uses besides vertebral disc annular fibrosis tensioning and lengthening devices, such as spinal fusion pedicle screw and rod instrumentation, well known to those skilled in the art. The holes 24 can come in a variety of numbers, diameters and configurations. In one non-limiting embodiment, the diameter of the body portion 12 is about 8 mm and the diameter of the holes is about 1.0 mm. The pedicle screw 10 can include a bore 26 that extends through the body portion 12 to make it cannulated so that a K-wire (not shown) can extend therethrough to allow for percutaneous placement of the pedicle screw over a K-wire that has previously been placed through the vertebral pedicle. This will allow for a minimally invasive application of the device that causes less disruption of the normal anatomical structures of the spine and improved recovery, as is well understood to those skilled in the art.

The pedicle screw 10 further includes a screw head 16 having an extended cup shape defining a cavity 18. The cavity 18 includes an open side 20 that fits a spring head (discussed below) and allows for mobility between the spring head and the cavity 18 of the screw head 16. This will permit mobility and will not limit flexion, extension and/or rotational mobility of the spine, thus allowing for the creation of a posterior motion-preserving device for reasons that will become apparent from the discussion below. An annular recess 22 is formed around an outside of the head 16 also for reasons that will become apparent from the discussion below. The pedicle screw 10 can be made of any suitable material, such as titanium, stainless steel, etc., as would be well understood to those skilled in the art. The cavity 18 could be made of ceramics or cobalt steel to limit wear between the spring head and the cavity 18.

FIG. 2 is a perspective view of a spring 30 having a cylindrical body 32 that is also part of the vertebral disc annular fibrosis tensioning and lengthening device. A series of slots 34 are cut into the body portion 32, as shown, in an alternating configuration that allows the body portion 32 to be compressed and provide an expansive spring force. The spring 30 includes generally rounded ends 36 and 38 that are shaped to conform to the shape of the inner surface of the cavity 18. The spring 30 can be made of any suitable material for the purposes described herein, such as nitinol, which is a flexible metal having a memory. Other materials may also be suitable, such as a shape memory alloy, polymers, hydrogels, etc., which could expand over time and allow for separation of the screw heads and disc height restoration. An example of a suitable alloy includes about 50% nickel and about 50% titanium.

Figure 4:
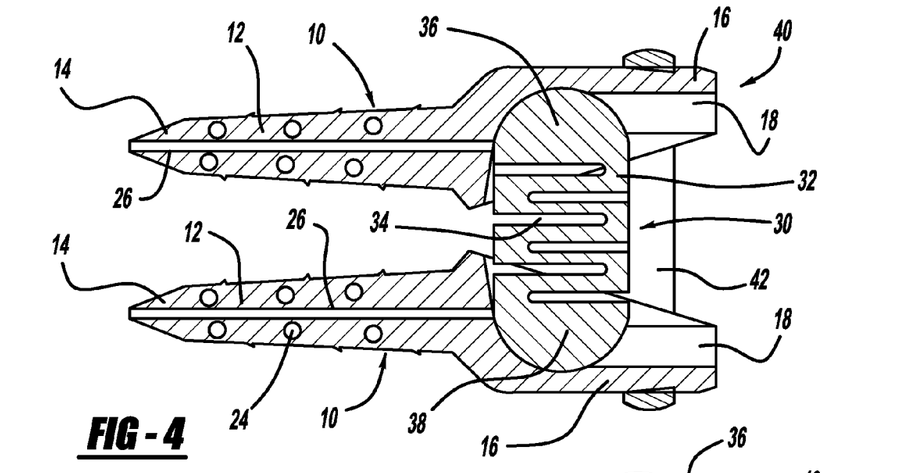
FIG. 4 is a cross-sectional side view of the vertebral disc annular fibrosis tensioning and lengthening device shown in FIG. 3.
Figures 5, 6:
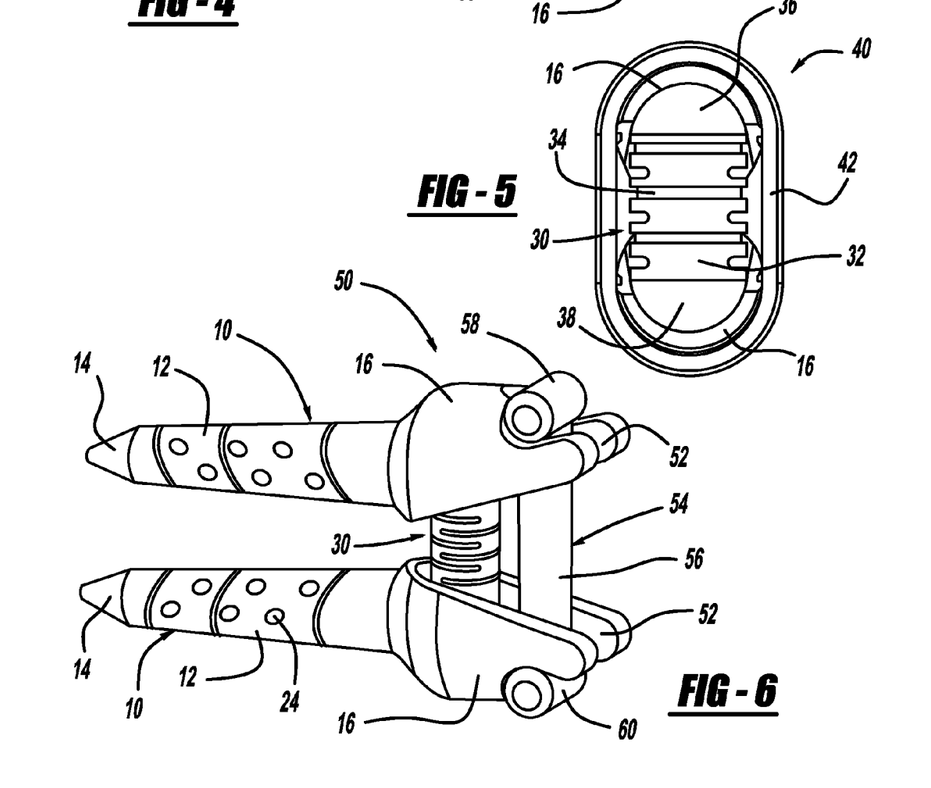
FIG. 5 is a top view of the vertebral disc annular fibrosis tensioning and lengthening device shown in FIG. 3.
FIG. 6 is a perspective view of a vertebral disc annular fibrosis tensioning and lengthening device, according to another embodiment.

FIG. 3 is a side view, FIG. 4 is a cross-sectional view, side view and FIG. 5 is a top view of a vertebral disc annular fibrosis tensioning and lengthening device 40, according to an embodiment. The vertebral disc annular fibrosis tensioning and lengthening device 40 includes two of the pedicle screws 10 where the open sides 20 of the heads 16 face each other, as shown. The spring 30 is inserted into the cavities 18 of the heads 16 so that the ends 36 and 38 conform to the inner surface of the cavities 18. The inner surface of the cavities 18 and the ends 36 and 38 can be coated with a suitable low friction material, such as chrome, cobalt, ceramic, etc., to prevent or reduce wear particle formation as the spring 30 and the pedicle screws 10 rub against each other. Initially, the spring 32 is compressed so that it provides an expansive force to separate the pedicle screws 10. In one non-limiting embodiment, the expanded or relaxed length of the spring 30 is in the range of about 3 cm-4 cm, which is about the height of a normal lumbar disc. The diameter of the spring 32 can be any diameter suitable for the purposes described herein.

An oval posterior ring 42 is positioned within the recesses 22, and operates to maintain the screws 10 in their proper orientation, and prevent the pedicle screws 10 from separating beyond a predetermined limit. The fixed diameter of the ring 42 allows for the tips 14 of the pedicle screws 10 to separate greater relative to the heads 16. This imparts lordosis. Further, as the spring 30 causes the pedicle screws 10 to separate, the ring 42 maintains the top end of the pedicle screws 10 stationary to create a pivot and restore the height of the disc and lordosis of the spine. Also, the configuration and orientation of the spring 30, the ring 42 and the screws 10 preserves the motion of the spine as the person performs normal physical movement in that it allows for continued flexion, extension, as well as axial rotation of the spine. The spring 30 operates as a compressible link and the posterior ring 42 operates as a rigid link.

FIG. 6 is a perspective view of a vertebral disc annular fibrosis tensioning and lengthening device 50, according to another embodiment, where like elements to the vertebral disc annular fibrosis tensioning and lengthening device 40 are identified by the same reference numeral. In this embodiment, the heads 16 of the pedicle screws 10 include a slot 52. The ring 42 is replaced with a dumbbell member 54 including a cylindrical body portion 56 and end portions 58 and 60. The body portion 56 extends through the slots 52 so that the end portions 58 and 60 are positioned on outside sides of the heads 16, and also operates to limit the expansion of the pedicle screws 10 and control the posterior aspects of the screws 10 and control the posterior aspects of the screws 10, thus allowing restoration of the lordosis, i.e., normal curvature, of the spine.

Figure 7:
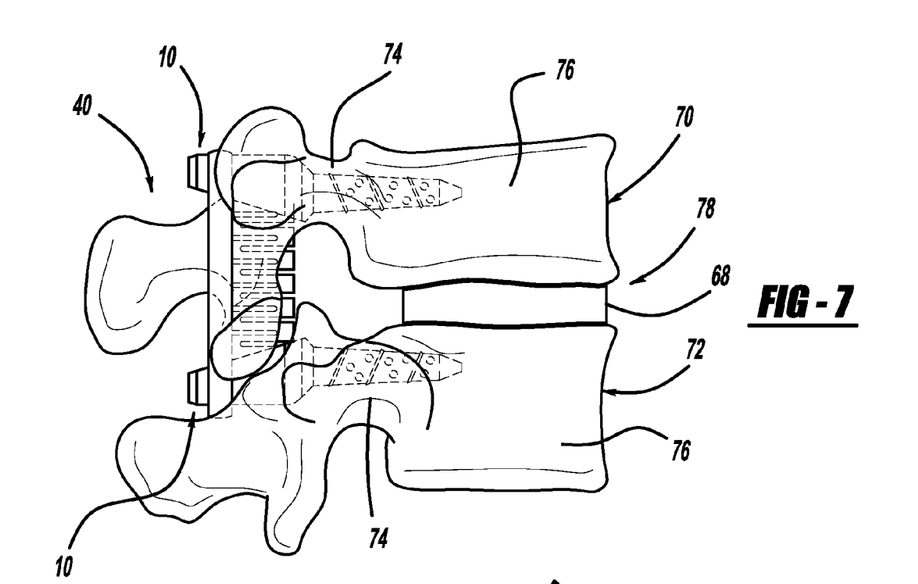
FIG. 7 is a side view showing a vertebral disc annular fibrosis tensioning and lengthening device of the invention inserted within adjacent vertebrae.
Figure 8:
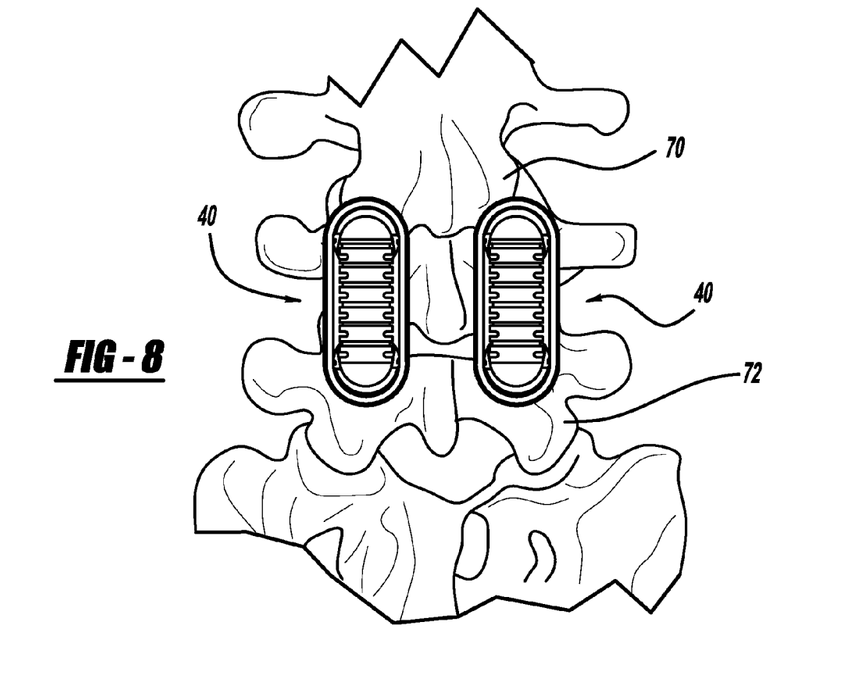
FIG. 8 is a top view of two vertebral disc annular fibrosis tensioning and lengthening devices of the invention inserted within the adjacent vertebrae.

FIG. 7 is a side view and FIG. 8 is a top view of two of the vertebral disc annular fibrosis tensioning and lengthening devices 40 coupled to two adjacent lumbar vertebra 70 and 72 having a disc 68 therebetween. The pedicle screws 10 are threaded through pedicles 74 of the vertebra 70 and 72 and into the vertebral body 76. Once the pedicle screws 10 are in place, then the spring 30 is positioned within the cavities 18 under compression, as discussed above. As the spring bias forces the vertebra 70 and 72 apart, the height of a disc space 78 between the vertebra 70 and 72 increases and is restored. Further, as the height of the disc space 78 increases, the disc 68 is able to regenerate due to reduced sheer or compressive forces applied to the disc 68. The device 40 creates a controlled distraction force and distraction distance on the annulus fibrosis and a controlled dynamic motion of the vertebra. Further, the device 40 allows motion of the spine while maintaining the stress tension effect on the disc 68. Particularly, the device 40 provides a tension force across a compromised vertebral disc providing a distractive force to elicit the stress tension effect on the annulus fibrosis. The pedicle screws and links therebetween are arranged in a parallelogram shape to provide the desired distraction. Because most systems work like a hinge, the front or anterior portion of the disc moves much more than the back or posterior portion of the disc. This is not a natural motion, so with the vertebral linkage of the invention, a parallel or near parallel motion of the disc can be achieved. In one non-limiting embodiment, the motion pathway is an arc of a radius much longer than the pedicle screw length. Although the device 40 is shown coupled to adjacent vertebra, the device 40 can extend across any suitable number of vertebrae to increase the disc space of more than one disc.

The device 40 can also be applied unilaterally to restore coronal alignment. This is particularly applicable to patients suffering from scoliosis where the curvature of the spine could be corrected by applying the device 40 to the concaved portion of the spine. Restoration of spinal alignment would ultimately open the neural foramina on the concaved side and help to alleviate symptoms of lower back pain experience by these patients.

Any suitable surgical procedure for placing the pedicle screws 10 can be used, including minimally invasive surgical procedures by making the pedicle screws 10 cannulated. In one known process of percutaneous pedicle screw instrumentation, a Jamshidi needle is used to dock on to the junction of the vertebrae between the facet complex and the transverse process of the vertebra. Gentle taps with a mallet cause the Jamshidi needle to be advanced through the pedicle 74, making sure not to cross the medial border of the pedicle 74, which can result in nerve root injury, until the junction between the pedicle base and the vertebral body is reached. Fluoroscopic visualization into the anterior posterior and lateral planes of the vertebra is used to see the orientation of the Jamshidi needle. The correct trajectory of the Jamshidi needle should place the tip of the needle in the center of the pedicle in the anterior posterior view when the tip of the Jamshidi needle lies at the pedicle vertebral body junction in the lateral view.

Once the junction between the base of the pedicle wall and the vertebral body is reached, the Jamshidi needle can be directed in a more medial fashion. The Jamshidi needle is typically passed to about one-half the depth of the vertebral body, and then a K-wire is passed down the Jamshidi needle and into the vertebral body a little farther to seat it into the bone. The Jamshidi needle is then removed. A series of cannulated muscle dilators are then passed over the K-wire to prevent the soft tissue from going into the threads of the tap. The pedicle is tapped and a cannulated pedicle screw is then passed down the dilators.

Although a specific type of spring has been described above for the vertebral disc annular fibrosis tensioning and lengthening device, the present invention contemplates any suitable linearly expandable link suitable for the purposes described herein. The link exerts a force creating a stress tension effect within the disc allowing it to regenerate according to Wolff's law. The link also allows parallel distraction of the disc, distraction along the coronal plane of the disc tissue, and puts the annulus fibrous in tension and provides torsional rotation of the vertebral construct. Further, the pedicle screws can be replaced with any suitable mounting member. By a more general description, the vertebral disc annular fibrosis tensioning and lengthening device includes a caudal vertebral body attachment member and a cephalad vertebral body attachment member having a non-rigid interconnection member therebetween that creates the tension stress effect on the annulus fibrosis. The posterior ring 42 acts as a rigid member coupled between the attachment members that also operates to provide the distractive force.

Figure 9:
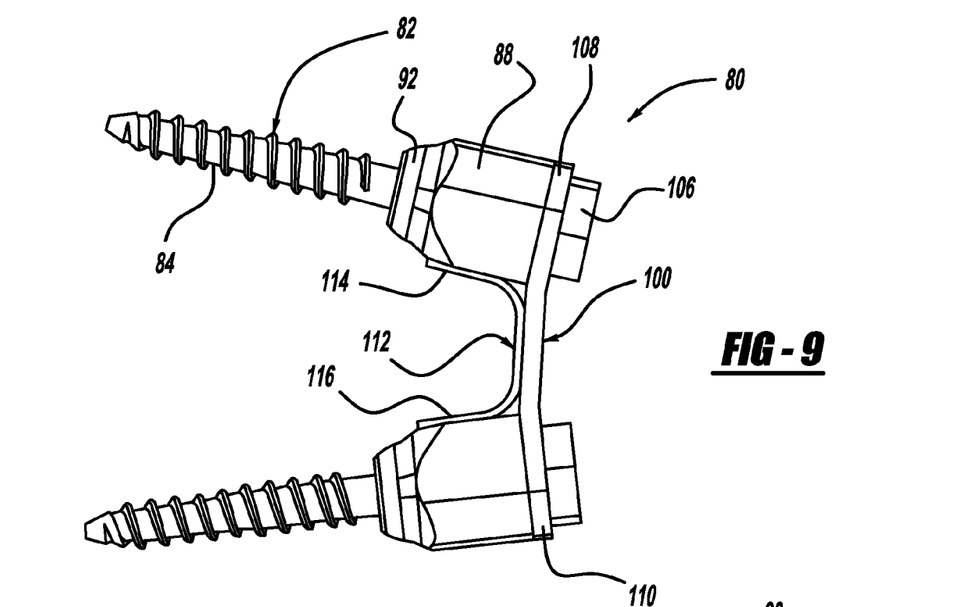
FIG. 9 is a perspective view of a vertebral disc annular fibrosis tensioning and lengthening device, according to another embodiment.
Figure 10:
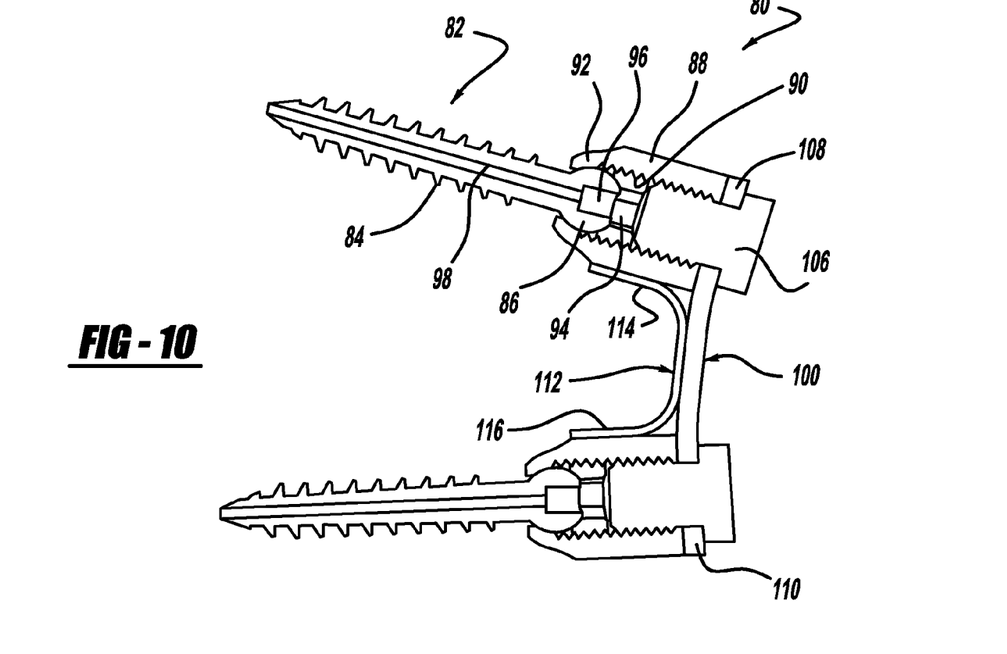
FIG. 10 is a cross-sectional view of the vertebral disc annular fibrosis tensioning and lengthening device shown in FIG. 9.

FIG. 9 is a perspective view and FIG. 10 is a cross-sectional view of a vertebral disc annular fibrosis tensioning and lengthening device 80, according to another embodiment, that illustrate other designs that provide the annular fibrosis tensioning and lengthening and restore the natural lordosis of the spine in the manner discussed above. The device 80 includes a pair of pedicle screws 82 each including a body portion 84 having a ball head 86. The pedicle screw 82 also includes a pedicle screw head portion 88 having an internal threaded bore 90 through which the body portion 84 extends so that the ball head 86 is mounted on a shoulder 92 within the bore 90, as shown. A collar 94 is threaded into the internal bore 90 of the pedicle screw head portion 88 and engages a slot 96 in the ball head 86 to rigidly hold the body portion 84 in place at a proper kyphotic angle. The body portion 84 includes an internal bore 98 that accepts the Jamshidi needle for the reasons discussed above.

Figures 11, 12:
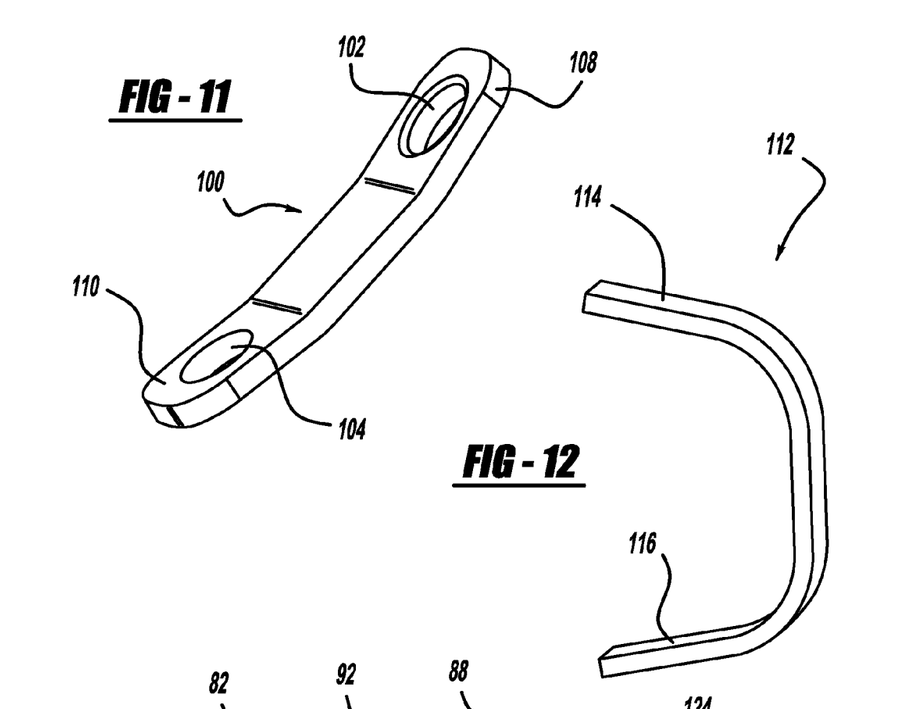
FIG. 11 is a perspective view of a plate member used in the device shown in FIGS. 9 and 10.
FIG. 12 is a perspective view of a spring element used in the device shown in FIGS. 9 and 10.

When the pedicle screws 82 are properly placed in the vertebrae during the surgical procedure, a plate connector 100, shown separated from the device 80 in FIG. 11, is positioned over the pedicle screw head portions 88 so that holes 102 and 104 in ends 108 and 110, respectively, in the plate connector 100 line up with the bores 90 in the pedicle screw head portions 88. Bolts 106 are then placed through the holes 102 and 104 and threaded into the threaded bores 90 in the pedicle screw head portions 88 to secure the plate connector 100 to the pedicle screws 82. The plate connector 100 has a gradual U-shape, as shown, where the ends 108 and 110 are slightly angled upward to provide the proper orientation for the device 80 that sets the maximum distraction of the disc.

In order to provide the distraction, a U-shaped spring element 112, shown separated from the device 80 in FIG. 12, is inserted between the pedicle screw head portions 88, where legs 114 and 116 of the spring element 112 push against the head portions 88, which cause the pedicle screw body portions 84 to pivot away from each other and cause the disc height to be restored in a lordotic manner. As the spring element 112 separates the pedicle screws 82 to provide the distraction, the pedicle screw head portions 88 pivot on the plate 100 to provide the desired distraction. Thus, the combination of the plate 100 and the spring element 112 provide the expandable and rigid link that operate in the manner as discussed above.

Figure 13:
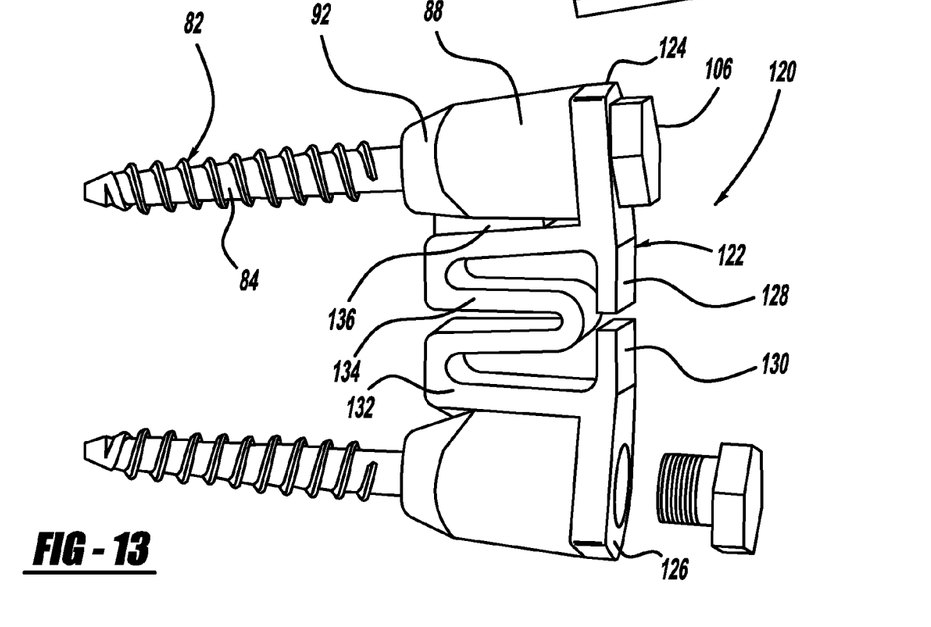
FIG. 13 is a perspective view of a vertebral disc annular fibrosis tensioning and lengthening device, according to another embodiment.

FIG. 13 is a perspective view of a vertebral disc annular fibrosis tensioning and lengthening device 120, according to another embodiment, where like elements to the device 80 are identified by the same reference numeral. In the device 120, the spring 112 and the plate 100 are combined or integrated into a single integrated element 122. The plate part of the integrated element 122 is flat in this embodiment and includes end pieces 124 and 126 through which the bolts 106 are placed. The element 122 includes limit stops 128 and 130 that limit the amount of distraction of the disc and also prevent overloading during jumping and other high loading states. The spring part of the integrated element 122 includes a live spring element 132 that provide the disc distraction. In this embodiment, an increased spring effect is provided by a spring loop portion 134 that extends the length of the spring element 132 to increase the distractive force.

The device 120 also includes an optional wedge member 136 positioned between one of the screw head portions 88 and the integrated element 122, as shown. The wedge 136 is placed by the surgeon to provide changes in both height and angulations simultaneously, if desirable.

Figure 14:
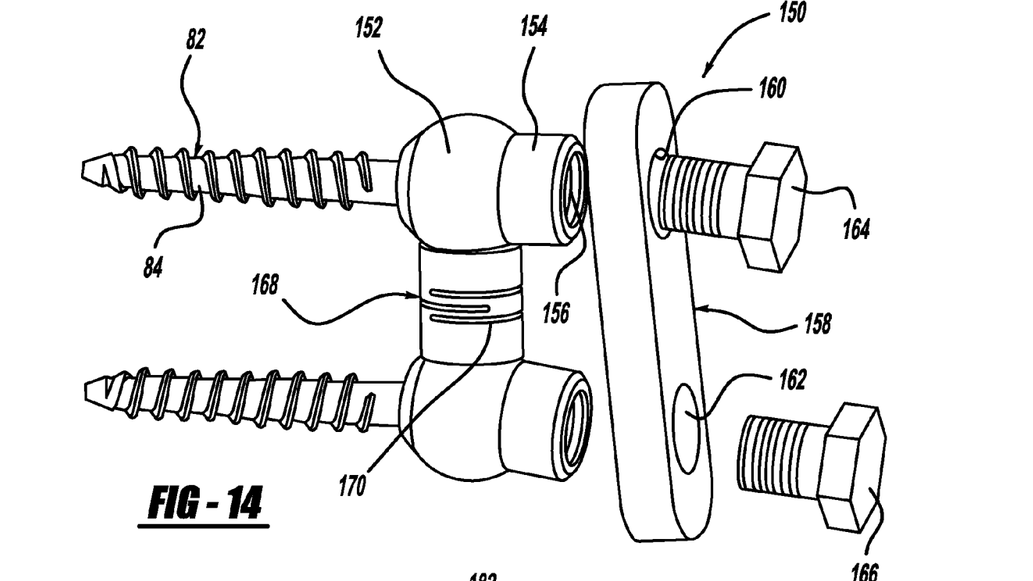
FIG. 14 is a broken-away, perspective view of a vertebral disc annular fibrosis tensioning and lengthening device, according to another embodiment.

FIG. 14 is a perspective view of a vertebral annular fibrosis tensioning and lengthening device 150, according to another embodiment, where like elements to the devices 80 and 120 are identified by the same reference numeral. In this embodiment, the screw head portion 88 is replaced with a rounded screw head portion 152. The screw head portion 152 includes a cylindrical cap portion 154 having an internal threaded bore 156. A plate 158 is mounted to the cap portions 154 so that holes 160 and 162 in the plate 158 line up with the bores 156. Bolts 164 are threaded into the bores 156 to secure the plate 158 to the screws 82. A cylindrical spring element 168 having spaced apart slots 170 is positioned between the rounded screw head portions 152, as shown, where the spring element 168 is held in place by the relative shape between the ends of the spring element 168 and the head portions 152. The spring element 168 provides the distractive force and the plate 158 provides the pivot limiting force as described above.

Figure 15:
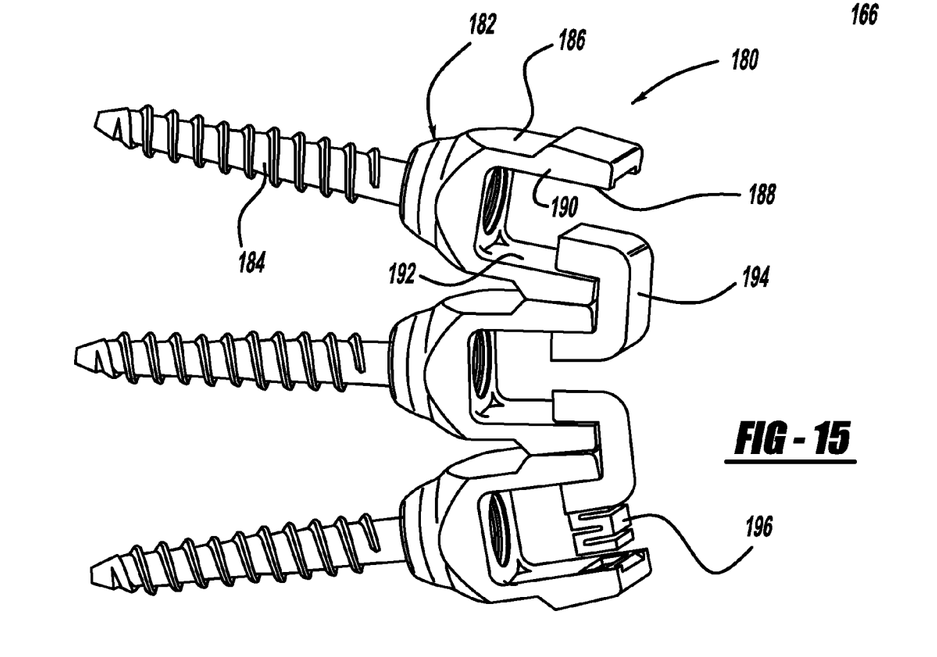
FIG. 15 is a perspective view of a disc height restoration assembly.

FIG. 15 is a perspective view of a disc height restoration assembly 180 including a plurality of pedicle screws 182 each including a body portion 184 and a head portion 186. The head portion 186 includes an open U-shaped channel 188 defining opposing side walls 190 and 192 that allow adjacent pedicle screws 182 to be positioned together, as shown. A clip member 194 is positioned over adjacent side walls 192 of adjacent pedicle screws 182 to clip the adjacent pedicle screws 182 together and provide a distracted force to the disc when the pedicle screws 182 are mounted to adjacent vertebrate. A spring element 196 is included.

Figure 16:
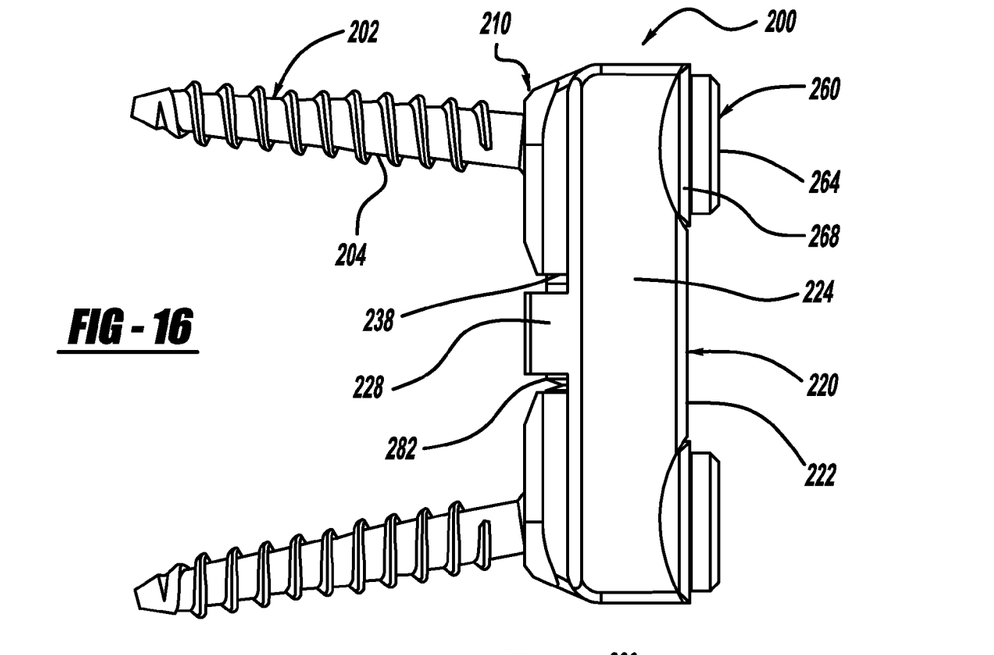
FIG. 16 is a side view of a vertebral disc tensioning device, according to another embodiment.
Figure 17:
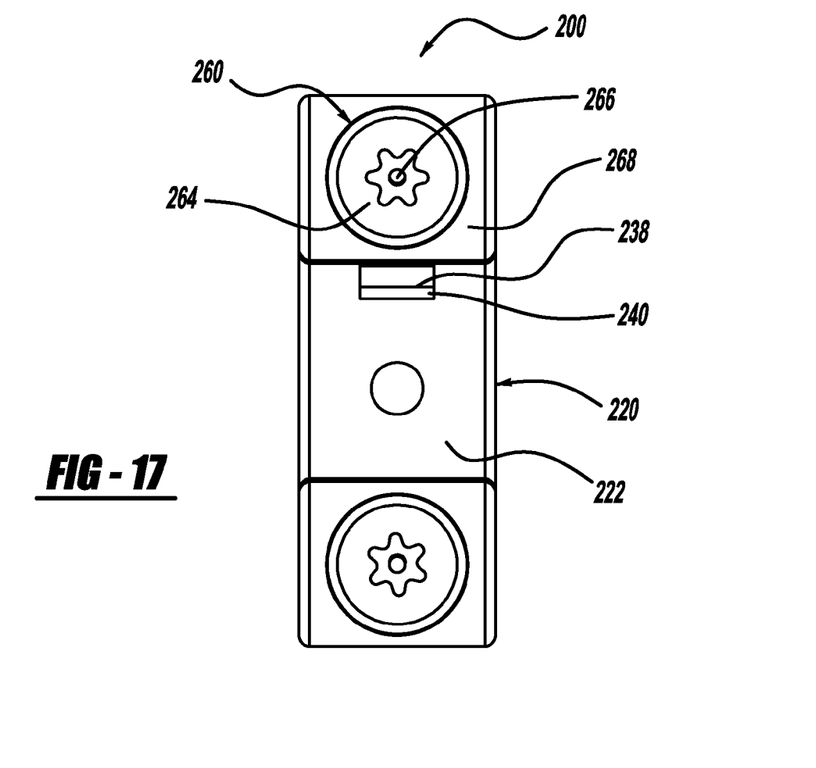
FIG. 17 is a top view of the device shown in FIG. 16.
Figure 18:
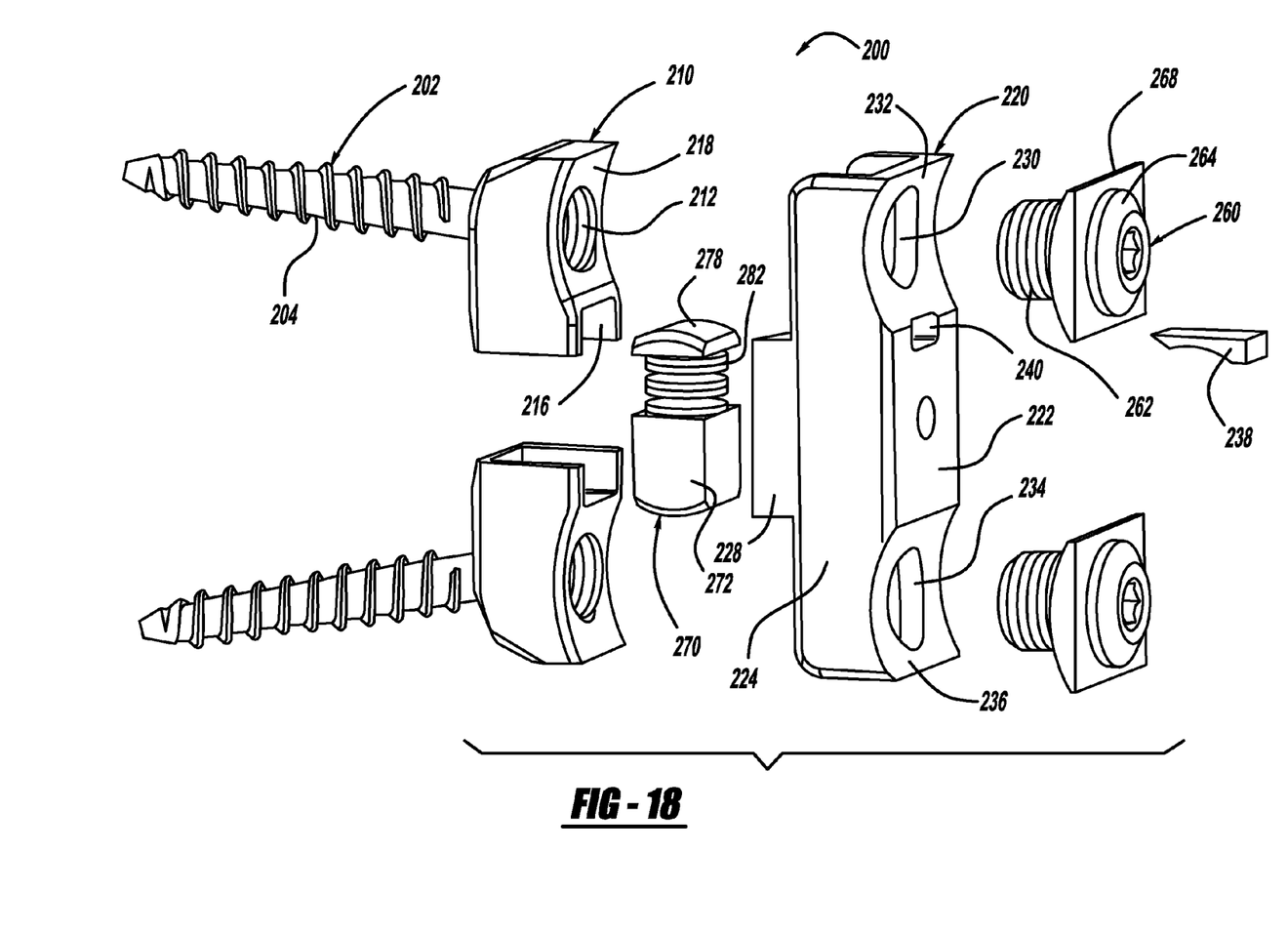
FIG. 18 is an exploded perspective view of the device shown in FIG. 16.
Figure 19:
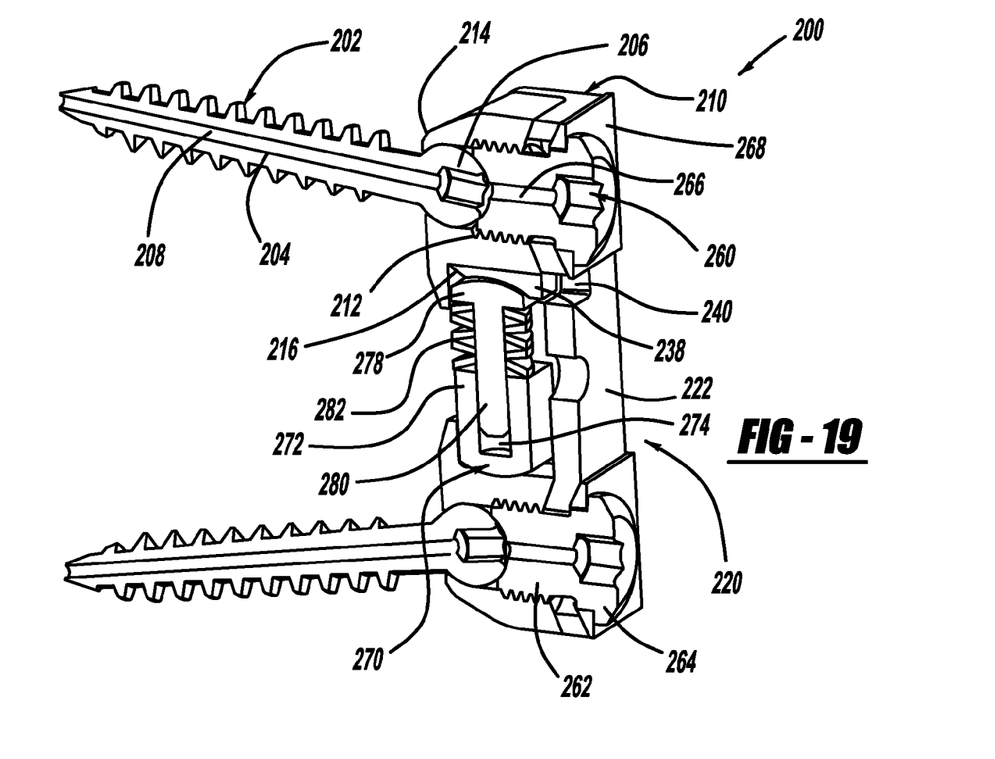
FIG. 19 is a cross-sectional view of the device shown in FIG. 16.
Figure 20:
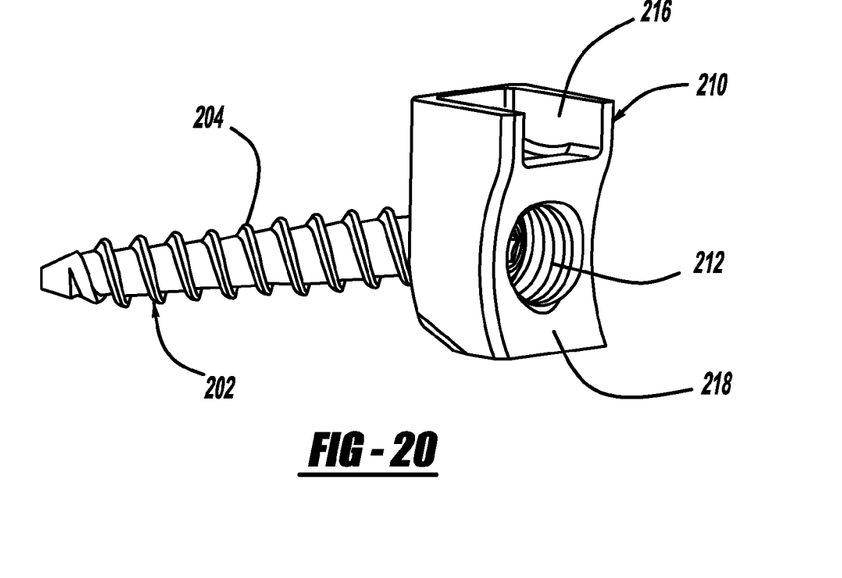
FIG. 20 is a perspective view of a pedicle screw and screw head portion in the device shown in FIG. 16.

FIG. 16 is a side view, FIG. 17 is a top view, FIG. 18 is a blown-apart perspective view and FIG. 19 is a cross-sectional perspective view of a vertebral disc annular fibrosis tensioning and lengthening device 200, according to another embodiment. The device 200 is operable to provide the disc tensioning and lengthening as discussed above to restore the natural lordosis of the spine. The device 200 includes a pair of pedicle screws 202 each having a body portion 204 and a ball head 206. An internal bore 208 extends through the body portion 206 and the ball head 206 to accept a K-wire as discussed above. The device 200 also includes a screw head portion 210 having an internal threaded bore 212. FIG. 20 is a perspective view of one of the pedicle screws 202 and one of the screw head portions 210 separated from the device 200. The body portion 204 of the screw 202 is inserted through a top end of the internal bore 212 until the ball head 206 rests against a narrowed shoulder 214 in the head portion 210 that allows the pedicle screw 202 to be pivoted relative to the screw head portion 210, as discussed above. The screw head portion 210 further includes a lateral cavity 216 that accepts a spring, as will be discussed in detail below. The screw head portion 210 also includes a concave shaped top surface 218 also provided for reasons that will become apparent for discussion below.

Figure 21:
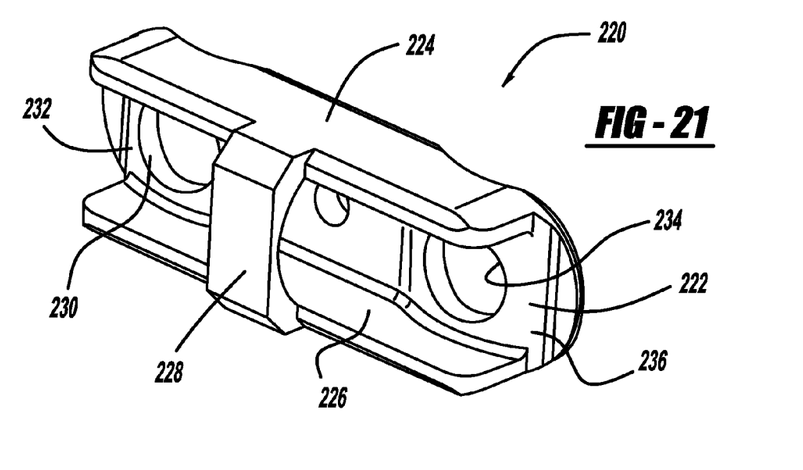
FIG. 21 is a connector in the device shown in FIG. 16.

The vertebral disc annular fibrosis tensioning and lengthening device 200 also includes a screw connector 220 shown separated from the device 200 in FIG. 21. The connector 220 includes a top plate 222 and opposing side plates 224 and 226, as shown. A support member 228 is connected to the opposing side plates 224 and 226 opposite to the top plate 222. In other words, the plates 224 and 226 are interconnected with a cross-link from a construct on one side of the spinal cord to the other. The connector 220 includes a first opening 230 provided in a convex shaped portion 232 at one end of the top plate 222 and a second opening 234 provided in a convex shaped portion 236 at an opposite end of the top plate 222 for reasons that will become apparent from the discussion below. The top plate 222 also includes a slot 240 through which a wedge 238 is inserted into the device 200 to adjust a spring travel, as will also be discussed below.

Figures 22, 23:
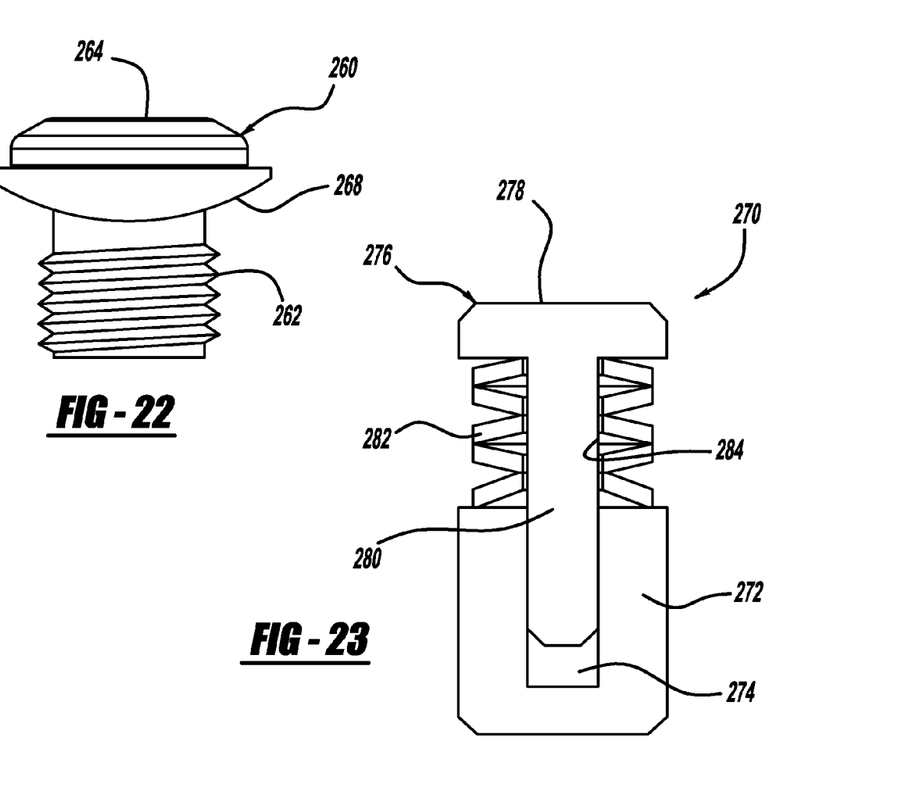
FIG. 22 is a bolt in the device shown in FIG. 16.
FIG. 23 is a spring assembly in the device shown in FIG. 16.

The device 200 also includes a pair of bolts 260, where one of the bolts 260 is shown separated from the device 200 in FIG. 22. The bolt 260 includes a bolt body 262 and a bolt head 264. An internal bore 266 extends through the bolt 260 and aligns with the bore 208 in the pedicle screw 202. A half-mooned shaped collar 268 including an opening extending therethrough is positioned around the bolt body 262 just below the bolt head 264 of the bolt 260, as shown.

The device 200 also includes a spring assembly 270 shown separated from the device 200 in FIG. 23. The spring assembly 270 includes a base portion 272 having a bore 274 therein. The spring assembly 270 also includes a plunger 276 having a cylindrical body portion 280 and a head portion 278. A compressible spring member 282 including an internal bore 284 is provided between the head portion 278 and the base portion 272 where the body portion 280 extends through the bore 284 and into the bore 274, as shown. A compression force between the plunger 276 and the base portion 272 causes the head portion 278 to push against the spring member 282 so that the body portion 280 extends farther into the channel 274.

The device 200 is assembled so that the pedicle screws 202 are pivotally mounted within the screw head portions 210 and the spring member 282 is positioned within the opposing cavities 216 of the head portions 210 so that the head portion 278 of the plunger 276 is in one of the cavities 216 and the base portion 272 is in the other cavity 216 of the other screw head portion 210. The connector 220 is then positioned over the screw head portions 210 so that the side plates 224 and 226 are provided at sides of the screw head portions 210 and the top plate 222 covers the cavities 216 to hold the spring assembly 270 within the device 200. In this configuration, the shape of the concave shaped portions 232 and 236 conforms to the concave surfaces 218 of the screw head portions 210. The bolts 260 are then threaded into the threaded openings 212 through the openings 230 and 234 to hold the connector 220 to the screw head portions 210. A bottom end of the bolts 260 is rounded to conform with the shape of the ball heads 206. Thus, the ball heads 206 can rotate within the screw head portions 210 on the shoulders 214. When the bolts 260 are threaded into the openings 212, the half-moon portions 268 conform to an upper surface of the concave portions 232 and 236. Thus, the connector 220 provides the non-compressible link and the spring assembly 270 provides the compressible link as discussed above to provide the disc distraction and regeneration. The wedge 238 can be driven through the hole 240 to conform with the head portion 278 of the plunger 276 to reduce the travel of the spring 282 if desired.

Figure 24:
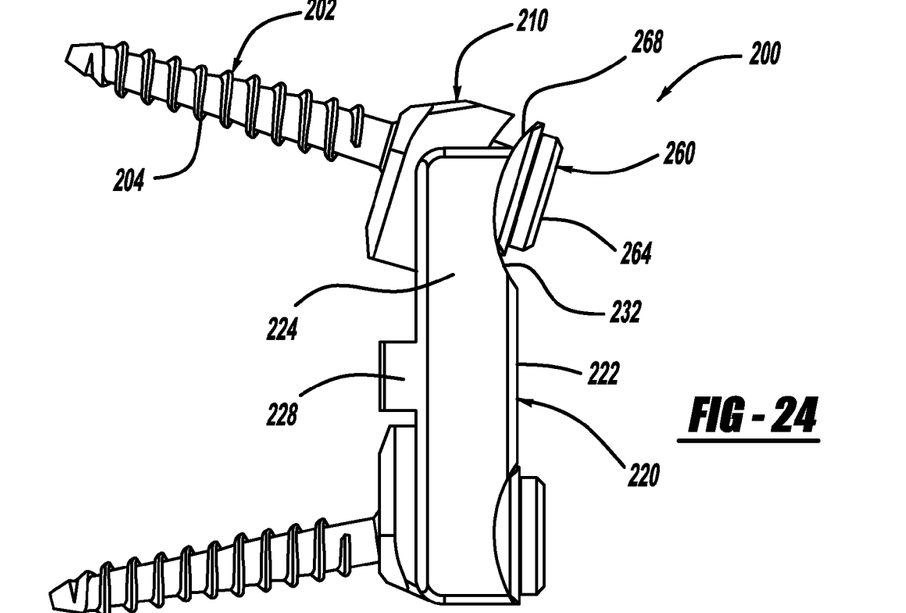
FIG. 24 is a side view of the device shown in FIG. 16 with the spring head portion pivoted relative to the connector.
Figure 25:
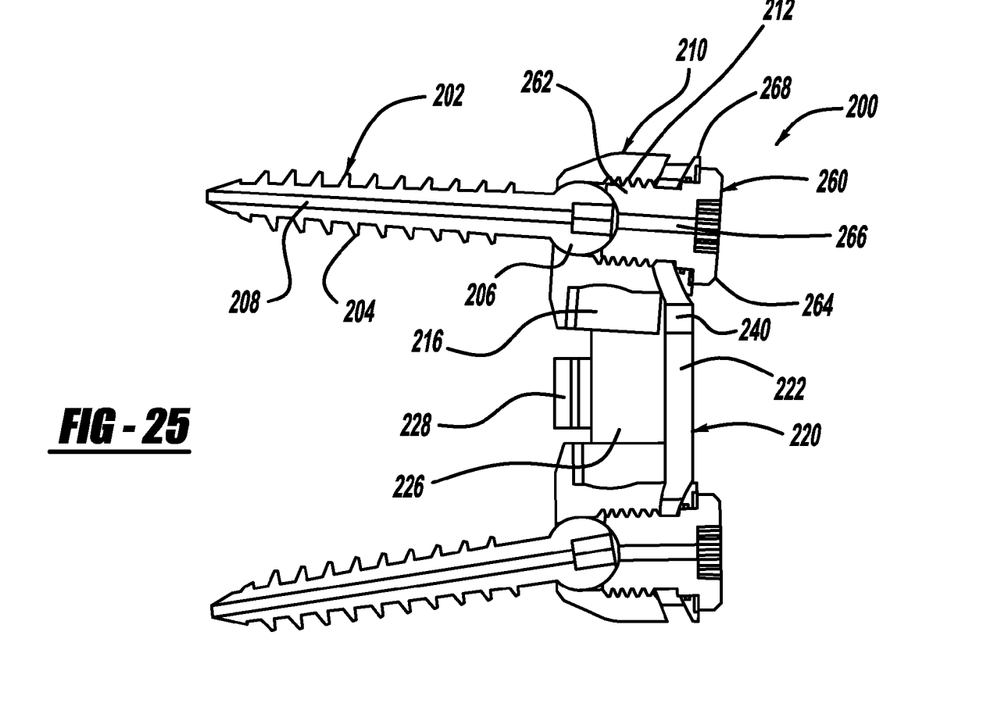
FIG. 25 is a cross-sectional view of the illustration shown in FIG. 24.

In addition to the pedicle screw 202 being able to pivot relative to the screw head portion 210, the assembly of the pedicle screw 202, the screw head portion 210 and the bolt 260 can pivot relative to the connector 220. FIG. 25 is a cross-sectional view of the device 200 with the spring assembly 270 removed and FIG. 24 is a side view of the device 200 showing this feature. As is apparent, the orientation and shaping of the concave surfaces 218 on the screw head portion 210, the concave shaped portions 232 and 236 of the plate connector and the half-moon shape of the collars 268 allow the spring head portions 210 and the collars 268 to pivot relative to the connector 222 when the bolt 260 is threaded into the threaded bore 212.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A vertebral disc annular fibrosis tensioning and lengthening device comprising:
   first and second screws each including a ball head and a screw body;
   first and second screw head portions each including an internal threaded bore and a shoulder therein, said first screw being inserted into the internal bore of the first screw head portion so that the ball head of the first screw is pivotally mounted on the shoulder of the first screw head portion so that the orientation of the first screw can be set relative to the first screw head and said second screw being inserted into the internal bore of the second screw head portion so that the ball head of the second screw is pivotally mounted on the shoulder of the second screw head portion so that the orientation of the second screw can be set relative to the second screw head;
   a connector coupled to the first and second screw head portions at a connector contact region; and
   a spring member positioned between and in contact with the first and second screw head portions at a spring contact region, said spring member being anteriorly offset from the connector, and configured so that spring member applies a bias force to the first and second screws that causes the screw body portions to separate at the spring contact region while the first and second screw head portions are held in place by the connector at the connector contact region.

2. The device according to claim 1 wherein the connector includes first and second openings, said device further comprising first and second bolts each including a bolt body and a bolt head, said first bolt extending through the first opening in the connector and being threadably engaged in the internal bore of the first screw head portion to be in contact with the ball head of the first screw and the second bolt extending through the second opening in the connector and being threadably engaged in the internal bore of the second screw head portion to be in contact with the ball head of the second screw.

3. The device according to claim 2 wherein the connector includes a top plate and opposing side plates defining a channel therebetween, said top plate including the first and second openings and said opposing side plates enclosing the first and second screw head portions, said first and second screw portions each including an opposing cavity, said spring member being positioned within the cavities and within the channel.

4. The device according to claim 3 further comprising a first convex shaped collar positioned around the first bolt body and a second convex shaped collar positioned around the second bolt body, said first collar being positioned within a first concave portion on the connector and said second collar being positioned within a second concave portion on the connector, said first screw head portion having a shaped surface that matches the first concave portion on the connector and said second screw head portion including a shaped surface that matches the second concave portion on the connector so that the first screw, the first screw head portion and the first bolt are operable to pivot together as a group relative to the connector and the second screw, the second screw head portion and the second bolt are operable to pivot together as a group relative to the connector.

5. The device according to claim 3 wherein the spring member is a spring assembly including a base portion having a bore, a plunger having a body portion and a head portion where the body portion is inserted into the bore of the base portion and a spring positioned between the plunger head and the base portion.

6. The device according to claim 5 wherein the top plate of the connector includes a slot, said slot accepting a wedge that is positioned between the head portion of the plunger and the first screw head portion.

7. The device according to claim 1 wherein the connector is a plate.

8. The device according to claim 7 wherein ends of the plate attached to the screw head portions are curved to cause ends of the screw body portions to point away from each other.

9. The device according to claim 7 wherein the spring member and the plate are integrated as a single member.

10. The device according to claim 9 wherein the integrated single member includes limit stops that oppose each other and limit the distance the screw body portions can separate.

11. The device according to claim 9 wherein the integrated single member includes a serpentine live spring portion.

12. The device according to claim 1 wherein the spring member is a U-shaped spring member where legs of the U-shaped spring member are positioned against the first and second screw head portions.

13. The device according to claim 1 wherein the first and second screw head portions include spherical portions and wherein the spring member is a cylindrical member positioned against the spherical portion of the first and second screw head portions.

14. The device according to claim 1 further comprising a collar threaded into the threaded bore of the screw head portions to hold the screw body portion in a predetermined position.

15. The device according to claim 1 wherein the ball head of the first and second screws has a slot, said device further comprising a set screw being inserted into the slot to hold the ball head against the shoulder and set the position of the screw.

16. The device according to claim 1 further comprising a wedge member positioned between one of the screw head portions and the spring member, said wedge member setting an angular orientation of the screw.

17. A vertebral disc annular fibrosis tensioning and lengthening device comprising:
    first and second screws each including a ball head and a screw body portion;
    first and second screw head portions each including an internal threaded bore and a tapered shoulder therein, said first screw being inserted into the internal bore of the first screw head portion so that the ball head of the first screw is pivotally mounted on the shoulder of the first screw head portion and said second screw being inserted into the internal bore of the second screw head portion so that the ball head of the second screw is pivotally mounted on the shoulder of the second screw head portion, said first and second screw head portions each including a cavity;
    a connector including a top plate and opposing side plates defining a channel therebetween, said top plate including first and second openings;
    first and second bolts each including a bolt body and a bolt head, said first bolt extending through the first opening in the top plate and being threadably engaged within the internal bore of the first screw head portion to be in contact with the ball head of the first screw and said second bolt being inserted through the second in the top plate and being threadably engaged within the internal bore of the second screw head portion to be in contact with the ball head of the second screw; and
    a spring assembly positioned within the channel of the connector and being positioned within the cavities of the screw head portions, said spring assembly providing a bias force that causes the screw body portions to separate.

18. The device according to claim 17 further comprising a first convex shaped collar positioned around the first bolt body and a second convex shaped collar positioned around the second bolt body, said first collar being positioned within a first concave portion on the connector and said second collar being positioned within a second concave portion on the connector, said first screw head portion having a shaped surface that matches the first concave portion on the connector and the second screw head portion including a shaped surface that matches the second concave portion on the connector so that the first screw, the first screw head portion and the first bolt are operable to pivot together as a group relative to the connector and the second screw, the second screw head portion and the second bolt are operable to pivot together as a group relative to the connector.

19. The device according to claim 17 wherein the connector includes a support portion coupled to the opposing side walls opposite to the top plate.

20. The device according to claim 17 wherein the spring assembly includes a base portion having a bore, a plunger having a body portion and a head portion where the body portion is inserted into the bore of the base portion and a spring member is positioned between the plunger head and the base portion.

21. The device according to claim 20 wherein the top plate of the connector includes a slot, said slot accepting a wedge that is positioned between the head portion of the plunger and the first screw head portion.

22. A vertebral disc annular fibrosis tensioning and lengthening device comprising:
    first and second screws each including a ball head and a screw body;
    first and second screw head portions each including an internal threaded bore and a shoulder therein, said first screw being inserted into the internal bore of the first screw head portion so that the ball head of the first screw is pivotally mounted on the shoulder of the first screw head portion and said second screw being inserted into the internal bore of the second screw head portion so that the ball head of the second screw is pivotally mounted on the shoulder of the second screw head portion;
    a connector coupled to the first and second screw head portions, said connector being a plate where ends of the plate attached to the screw head portions are curved to cause ends of the screw body portions to point away from each other; and
    a spring member positioned between and in contact with the first and second screw head portions, said spring member being anteriorly offset from the connector, said spring member applying a bias force to the first and second screws that causes the screw body portions to separate at a spring contact region while the first and second screw head portions are held in place by the connector at a connector contact region.

23. A vertebral disc annular fibrosis tensioning and lengthening device comprising:
    first and second screws each including a ball head and a screw body;
    first and second screw head portions each including an internal threaded bore and a shoulder therein, said first screw being inserted into the internal bore of the first screw head portion so that the ball head of the first screw is pivotally mounted on the shoulder of the first screw head portion and said second screw being inserted into the internal bore of the second screw head portion so that the ball head of the second screw is pivotally mounted on the shoulder of the second screw head portion;

a connector coupled to the first and second screw head portions; and a spring member positioned between and in contact with the first and second screw head portions, said spring member being anteriorly offset from the connector, said spring member applying a bias force to the first and second screws that causes the screw body portions to separate at a spring contact region while the first and second screw head portions are held in place by the connector at a connector contact region, said connector being a plate where the spring member and the plate are integrated as a single member.

24. A vertebral disc annular fibrosis tensioning and lengthening device comprising:

first and second screws each including a ball head and a screw body;

first and second screw head portions each including an internal threaded bore and a shoulder therein, said first screw being inserted into the internal bore of the first screw head portion so that the ball head of the first screw is pivotally mounted on the shoulder of the first screw head portion and said second screw being inserted into the internal bore of the second screw head portion so that the ball head of the second screw is pivotally mounted on the shoulder of the second screw head portion;

a connector coupled to the first and second screw head portions; and a spring member positioned between and in contact with the first and second screw head portions, said spring member being anteriorly offset from the connector, said spring member applying a bias force to the first and second screws that causes the screw body portions to separate at a spring contact region while the first and second screw head portions are held in place by the connector at a connector contact region, wherein the spring member is a U-shaped spring member where legs of the U-shaped spring member are positioned against the first and second screw head portions.

25. A vertebral disc annular fibrosis tensioning and lengthening device comprising:

first and second screws each including a ball head and a screw body;

first and second screw head portions each including an internal threaded bore and a shoulder therein, said first screw being inserted into the internal bore of the first screw head portion so that the ball head of the first screw is pivotally mounted on the shoulder of the first screw head portion and said second screw being inserted into the internal bore of the second screw head portion so that the ball head of the second screw is pivotally mounted on the shoulder of the second screw head portion wherein the ball head of the first and second screws has a slot;

a set screw being inserted into the slot to hold the ball head against the shoulder and set the position of the screw;

a connector coupled to the first and second screw head portions; and a spring member positioned between and in contact with the first and second screw head portions, said spring member being anteriorly offset from the connector, said spring member applying a bias force to the first and second screws that causes the screw body portions to separate at a spring contact region while the first and second screw head portions are held in place by the connector at a connector contact region.

* * * * *